United States Patent [19]
Schulte-Elte et al.

[11] 3,966,819
[45] June 29, 1976

[54] SESQUITERPENIC DERIVATIVES AS ODOR- AND TASTE MODIFYING AGENTS

[75] Inventors: Karl-Heinrich Schulte-Elte, Onex-Geneva; Michel Joyeux, Carouge-Geneva; Günther Ohloff, Bernex-Geneva, all of Switzerland

[73] Assignee: Firmenich S.A., Geneva, Switzerland

[22] Filed: Aug. 21, 1974

[21] Appl. No.: 499,120

[30] Foreign Application Priority Data
Sept. 5, 1973 Switzerland.................. 12784/73

[52] U.S. Cl. .......................... 260/586 F; 252/522; 260/586 R
[51] Int. Cl.[2]................. C07C 45/02; C07C 49/61
[58] Field of Search............................ 260/586 F

[56] References Cited
UNITED STATES PATENTS 3,678,119  7/1972  Kitchens et al................ 260/586 F
3,708,528  1/1973  Mukherjee et al. ............. 260/586 F
3,754,037  8/1973  Kitchens et al................ 260/586 F

OTHER PUBLICATIONS

Olah, "Friedel–Crafts and Related Reactions," pp. 129–134 (1963).
Mickon, "J.A.C.S.," 77, pp. 1190–1196 (1955).
Sorm et al., "Chem. Ab.," vol. 45, p. 8482b (1951).

*Primary Examiner*—Norman Morgenstern
*Attorney, Agent, or Firm*—Pennie & Edmonds

[57] ABSTRACT

New oxygenated sesquiterpenic derivatives useful as perfuming and odor-modifying agents in the manufacture of perfumes and perfumed articles, and as flavoring and taste-modifying agents in the aromatization of foodstuffs in general and imitation flavors for foodstuffs, animal feeds, beverages, pharmaceutical preparations and tobacco products.

Novel process for the preparation of said compounds and compositions of matter relating to mixtures containing same.

3 Claims, No Drawings

SESQUITERPENIC DERIVATIVES AS ODOR- AND TASTE MODIFYING AGENTS

SUMMARY OF THE INVENTION

The compounds to which the present invention relates belong to the class of oxygenated derivatives of the sesquiterpene hydrocarbons of formula

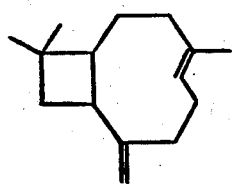

Ia (caryophyllene)

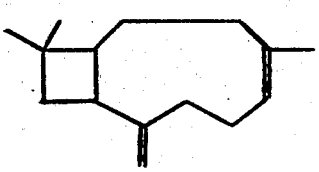

Ib (iso-caryophyllene)

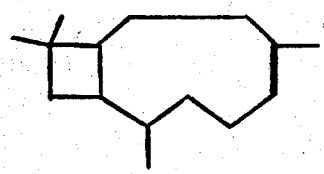

Ic (iso-dihydrocaryophyllene)

and

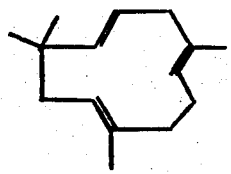

Id (humulene)

The compounds of the invention are prepared by a process comprising the reaction between one of said sesquiterpene hydrocarbons or any mixture thereof, and an acetylating reagent in the presence of an acid catalyst. The following are specific examples of the compounds of the invention:

5-acetyl-2,6-dimethylene-10,10-dimethylbicyclo [7.2.0$^{1,9}$]undecane 1-acetyl-11-methylene-4,7,7-trimethyl-cycloundeca-4,8-diene.

The compounds of the invention possess interesting organoleptic properties and, accordingly, are useful as perfuming and odour-modifying agents, and as flavouring and taste-modifying agents, and as flavouring and taste-modifying agents.

The present invention relates also to compositions of matter relating to mixtures containing same and to a process for modifying, enhancing or improving the odoriferous properties of perfumes and perfumed products, or the flavouring properties of foodstuffs, animal feeds, beverages, pharmaceutical preparations or tobacco products, which process comprises adding thereto an olfactive and/or flavouring amount of at least one of the compounds prepared according to the afore mentioned chemical process.

BACKGROUND OF THE INVENTION

In the art of perfumery, particularly, great attention was being devoted in the past to the utilization of caryophyllene, as well as to the preparation of certain of its derivatives. Caryophyllene, in fact, possesses a typical woody fragance note reminiscent of that developed by cedar wood [see e.g., A. Müller, Internationaler Riechstoff Kodex, Dr. A. Hüthig Verlag, Heidelberg (1969)]. Its epoxide derivative of formula

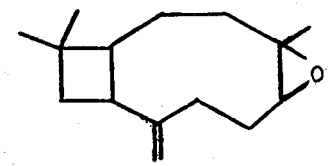

as well as its hydroxy-derivatives of formula

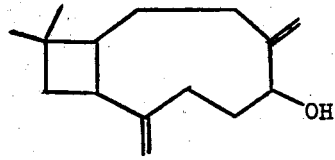

and

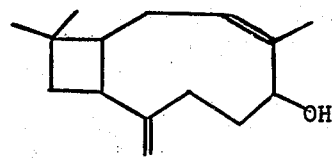

are useful ingredients for the aromatization of tobacco [see laid open to public inspection German application No. 2,202,066]. Equally, caryophyllene acetate having the formula

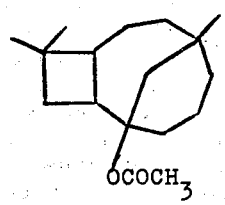

is known in the art for its green, woody-fruity character [see : S. Arctander, Perfume and Flavor Chemicals, Montclair, N.J. (1969), sect. 595 ].

THE INVENTION

We have now discovered that the reaction product obtained by treating a sesquiterpene hydrocarbon selected from the group consisting of the compounds of formula I*a*, I*b*, I*c* and I*d*, or any mixture thereof, with an acetylating reagent in the presence of an acid catalyst, develops very useful organoleptic properties and, accordingly, it is an object of the present invention to provide compositions of matter essentially consisting of, or comprising the said product.

The organoleptic properties of the said product greatly differ from that of the afore mentioned prior known derivatives. The compounds of the invention possess in fact a well defined clinging woody note which enables particularly harmonious matches with a great variety of coingredients in different perfuming and flavouring compositions. Owing particularly to the absence of the unpleasant terpenic nuance shown by caryophyllene, their woody character is remarkably elegant and their use is therefore much broader in scope than that of the prior known compounds.

When the compounds of the invention are used as flavouring ingredients, they are especially appreciated for their woody and sweety gustative note. These flavouring characters are suitable for the aromatization of foodstuffs such as jams, puddings, bakery or confectionery products, and beverages such as fruit syrups.

The term "foodstuff" is used here broadly, and includes coffee, tea and chocolate.

Interesting flavouring effects can be achieved with proportions ranging from about 2 to 500 ppm, preferably from 2 to 20 ppm of the compounds of the invention, based on the weight of the product flavoured. For the aromatization of tobacco, the proportions may typically be comprised in between 50 and 500 ppm; but amounts higher than those indicated can be used for special effects. When the compounds of the invention are used in flavouring compositions, in mixtures with other flavouring agents, they may typically constitute up to 80% of the total weight of the flavouring composition.

When used as perfuming agents, the compounds of the invention can be used at concentration of between about 0.5 to 1% by weight of the total weight of the composition to which they are added. Preferentially, however, these proportions are of between about 1 and 10%.

When used as perfuming ingredients in perfumed articles, such as soaps, cosmetics, detergents, waxes, bleaching powders and household materials in general, their concentrations can be much smaller than those above indicated and being of about 0.01 to 0.1% by weight, based on the weight of the perfumed article. In accordance with the present invention, the acetylation can be carried out on the sesquiterpene hydrocarbons of formula I*a*, I*b*, I*c* and I*d* either individually in their pure isomeric form or in admixtures comprising at least two of them, in any desired proportions relative to each other. Although all the thus obtained products possess an interesting harmonious olfactive and gustative woody note, the products obtained by acetylation of caryophyllene and humulene, or any mixture thereof, are of major interest, their character being the strongest and most elegant of all. For practical and economical reasons, the most advantageous method comprises the direct acetylation of the mixture of sesquiterpene hydrocarbons as obtained by simple distillation of the terpene fraction separated from clove oil. Due to the presence in it of appreciable amounts of eugenol, this commercially available essential oil has to be subjected to a preliminary treatment with a base, e.g. sodium hydroxide, followed by a fractional distillation. In our experience, the fraction having b.p. 80°–110°C/2 Torr represents the most suitable starting material for the process of the invention.

The individual pure compounds of formula I, particularly I*a* and I*d*, i.e. caryophyllene and humulene, respectively, which are compounds of natural origin, can be separated from the clove oil, obtained from Eugenia Caryophyllata by several subsequent fractional distillations.

Compound I*b*, better known as iso-caryophyllene, can be synthesized starting from caryophyllene by a photochemical reaction as shown by Schulte-Elte et al in Helvetica Chimica Acta 51, 494 (1968). The product thus obtained can be subjected to a catalytic hydrogenation in the presence of Raney-nickel to give iso-dihydrocaryophyllene of formula I*c*.

According to a preferred embodiment of the process of the invention, acetic anhydride is the most suitable acetylating reagent. Suitable acid catalyst include protic acid such as mineral or organic acids, e.g. phosphoric or p-toluene-sulfonic acid, an acidic diatomaceous earth or a Lewis acid such as $BF_3$, $AlCl_3$, $SnCl_4$ or $ZnCl_2$. Phosphoric acid or $ZnCl_2$ are preferred. The temperature at which the reaction is carried out, may vary within a wide range. Typically, it is of between about 40° and 100°C, preferably of from 40° to 80°C. The reaction time can equally vary widely and be comprised from about 2 to about 7 hours depending on a variety of factors. However, it has been observed that a reaction time of 3 hours is sufficient in most cases to promote a satisfactory conversion whenever the process is effected on an industrial scale.

We have analyzed in detail the composition of the products obtained by the acetylation of caryophyllene or humulene, whenever said acetylation was achieved in the presence of a Lewis acid under the conditions of a Friedel-Crafts reaction. A careful fractional distillation of the obtained reaction product followed by a deep spectral analysis allowed assigning to the product in question the formula

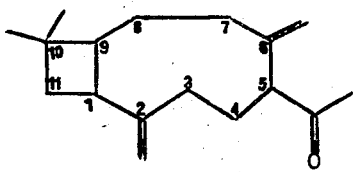

IIa (5-acetyl-2,6-dimethylene-10,10- dimethylbicyclo$[7.2.0^{1,9}]$undecane when caryophyllene was used as starting material, and the formula

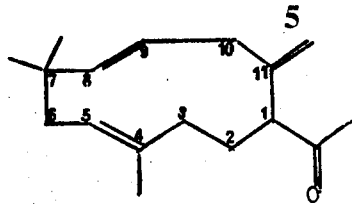

IId (1-acetyl-11-methylene-4,7,7-tri-methyl-cycloundeca-4,8-diene)

NMR : 1.0 (6H, 2s); 2.0 (3H, s); 4.75–4.95 (4H, complex band) δ ppm

MS : $M^+ \mp 246$ (1); m/e : 231 (3); 203 (10); 161 (30); 147 (30) 119 (70); 91 (35); 69 (42); 43 (100).

The acetylation of iso-caryophyllene as well as iso-dihydrocaryophyllene can be effected in accordance with the same process. The reaction conditions used and the yields respectively obtained in the course of different experiments are shown in the following table:

TABLE

| | Hydrocarbon (M) | Acetic anhydride (M) | Catalyst (M) | Time/Temperature (h) (°C) | Yield ca. % |
|---|---|---|---|---|---|
| | Caryophyllene | | | | |
| a | 0.50 | 4.0 | $H_3PO_4$ (poly-) : 0.1 | 7/60 | 61 |
| b | 0.25 | 0.75 | $ZnCl_2$ : 0.01 | 4/60 | 80 |
| c | 0.50 | 1.5 | $ZnCl_2$ : 0.04 | 3/60 | 81 |
| | Iso-Caryophyllene | | | | |
| d | 0.50 | 0.5 | $H_3PO_4$(poly-) : 0.1 | 7/100 | 50 |
| e | 0.25 | 1.0 | $H_3PO_4$ : 0.08 | 7/80 | 68 |
| | Iso-Dihydrocaryophyllene | | | | |
| f | 0.01 | 0.03 | $ZnCl_2$ : 0.01 | 7/80 | 60 | when humulene was used instead.

The present invention relates also to these two novel compounds, as well as to their use as perfuming and flavouring agents. The invention is better illustrated by but not limited to the following examples wherein the temperature are indicated in degrees centigrade. In the said examples the abbreviations have the meaning common in the art.

EXAMPLE 1

100 g of caryophyllene, the purity of which was of about 98%, were poured into a mixture comprising 400 g of acid anhydride and 10 g of polyphosphoric acid and the mixture was kept under stirring in a nitrogen atmosphere at about 60° for 7 hours. After cooling the reaction mixture was poured onto crushed ice and extracted with diethyl ether. The combined organic extracts were washed with a 10 % aqueous sodium bicarbonate solution, then with water until neutrality.

After evaporation of the volatile portions, a fractional distillation of the obtained residue (120 g) by means of a Vigreux column gave 72 g (61 %) of a fraction having b.p. 75°–130°/0.01 Torr; $n_D = 1.5191$; $d^{20} = 1.105$ This fraction comprised a mixture containing several compounds which can be separated each from the other by means of vapour phase chromatography by using a CARBOWAX column of 1 m length at 200°.

By means of several subsequent fractional distillations followed by vpc separations it was possible to isolate a product having a purity of ca. 95 % as shown by vpc; said product showed the following analytical data:

B.p. 80°–2°/0.1 Torr; $n_D = 1.5009$; $d^{20} = 0.9679$
$α_D = -1°$
IR : 3085, 1790, 1710 and 1640 $cm^{-1}$ The respective analytical data of the products thus obtained were the following:

a. B.p. 75°–130°/0.01 Torr; $n_D = 1.5191$; $d^{20} = 1.015$
b. B.p. 75°–130°/0.01 Torr; $n_D = 1.5005$; $d^{20} = 1.026$
c. B.p. ca. 75°–130°/0.01 Torr; $n_D = 1.5002$; $d^{20} = 1.013$
d. B.p. 75°–130°/0.01 Torr; $n_D = 1.5191$; $d^{20} = 1.015$
e. B.p. 85°–115°/0.01 Torr; $n_D = 1.5102$; $d^{20} = 1.001$; $α_D = -58.1°$
f. B.p. 80°–125°/0.01 Torr; $n_D = 1.4964$; $d^{20} = 0.9854$

EXAMPLE 2

10 g of pure humulene, which can be obtained by separation by means of serveral subsequent fractional distillations from the terpene fraction isolated from a commerically available clove oil, were treated with 15 g of acetic anhydride in the presence of 0.5 g of $ZnCl_2$ in a nitrogen atmosphere at about 60°. After ca. 2½ hours a conversion of about 85% of the starting humulene was observed and the reaction mixture was poured onto crushed ice and subjected to the same treatments as indicated in Example 1.

By fractional distillation of the residue obtained by extraction and subsequent evaporation of the volatile portions, 10.6 g of a mixture comprising about 70% of 1-acetyl-11-methylene-4,7,7-trimethyl-cycloundeca-4,8-diene were obtained. An analytical sample of said product showed the following analytical data:

$n_D = 1.5061$; $d^{20} = 0.9598$;
IR : 3085, 1710, 1640, 975 and 895 $cm^{-1}$;
NMR : 1.1 (6H, 2S); 1.52 (3H, s); 2.0 (3H, s); 4.65 and 4.9 (2H, 2m); 5.0 (1H, m); 5.1 (2H, m) δ ppm.
MS : $M^+ = 246$ (10); m/e : 231 (5); 203 (25); 147 (15); 135 (18); 119 (20); 109 (35); 81 (30); 69 (25); 43 (100).

EXAMPLE 3

800 g of the terpene fraction of clove oil having b.p. 80°–110°/2Torr, preliminary treated with sodium hydroxide, were heated with 1040 g of acetic anhydride in the presence of 40 g of anhydrous zinc chloride. The acetic anhydride was added to the clove oil portionwise at such a rate as to avoid a too rapid increase of temperature which was kept at about 45° by external cooling. The reaction mixture was then kept under stirring at room temperature during 12 hours, then 400 g of diethyl ether were added thereto. The organic phase was washed 3 times with 250 ml fractions of water then once with 250 g of a 10% aqueous solution of sodium bicarbonate. After evaporation of the volatile portions, 621 g of a fraction having b.p. 99°–147°/0.01 Torr were obtained. This fraction comprised in a proportion of about 50% 5-acetyl-2,6-dimethylene-10,10-dimethylbicyclo [7.2.0$^{1,9}$]undecane.

The odoriferous properties of the obtained mixture were judged as being perfectly suited for a direct industrial application of the said mixture.

EXAMPLE 4

A base perfume composition of the "tobacco" type was obtained by mixing together the following ingredients (parts by weight):

| | |
|---|---|
| Synthetic bergamot oil | 180 |
| Benzyl salicylate | 70 |
| Synthetic civet "Tinktur" 10 %* | 70 |
| Absolute oak moss 10 %* | 70 |
| Benjoin resinoid of Siam 50 %* | 60 |
| Coumarin | 60 |
| Ambrette musc | 50 |
| Snythetic absolute rose of may | 50 |
| Cyclopentadecanolide 10 %* | 50 |
| α-Isomethylionone | 40 |
| Amyl salicylate | 40 |
| Heliotropin | 40 |
| Geranium oil of Africa | 30 |
| Lavender oil | 30 |
| Isobutyl benzoate | 30 |
| Eugenol | 20 |
| Linalyl acetate | 20 |
| Synthetic absolute orange flowers | 20 |
| Lemon oil | 10 |
| Patchouli oil | 10 |
| Isoeugenol | 10 |
| α-Ionone | 10 |
| Nonanal 10 %* | 10 |
| Decanal 10 %* | 10 |
| 1,6,10,10-Tetramethyl-2-oxa-tricyclo[8.3.0.0$^{6,11}$]tridecane 0.1 %* | 10 |
| Total | 1000 |

*in diethyl phthalate

A novel composition was obtained by adding 10 g of 5-acetyl-2,6-dimethylene-10,10-dimethylbicyclo[7.2.0$^{1,9}$] undecane to 90 g of the above indicated perfume base composition. Said novel composition possessed a more distinct, elegant and clinging woody note than that of the base composition. It possesses moreover a better fragrance harmony.

By replacing the afore mentioned undecane by 1-acetyl-11-methylene-4,7,7-trimethylcycloundeca-4,8-diene analogous effects were observed.

For any practical application, however, 5-acetyl-2,6-dimethylene-10,10-dimethylbicyclo-[7.2.0$^{1,9}$] undecane can be replaced by the mixtures as directly obtained by the chemical process of the invention, namely described in Examples 1 and 3 above. The odoriferous effects so achieved were analogous to those observed by the use of the individual pure compounds afore mentioned.

EXAMPLE 5

100 g of "American blend" tobacco were sprayed with 7 g of a 1% solution of 5-acetyl-2,6-dimethylene-10,10-dimethylbicyclo[7.2.0$^{1,9}$] undecane in 95% ethanol. The tobacco thus flavoured was used to manufacture test cigarettes. As a control, cigarettes were also manufactured from the same tobacco sprayed with 95% ethanol alone. The smoke from the cigarettes was subjected to organoleptic evaluation by a panel of flavour experts, who unanimously stated that the smoke of the flavoured cigarettes possessed a sweeter character than that of the control cigarettes and presented moreover a woody note reminiscent of that developed by cedar wood. Analogous effects were observed when the mentioned undecane was replaced by mixtures as directly obtained by the process of the invention, namely described in Examples 1 and 3.

What is claimed is:

1. A process for preparing perfume ingredients consisting essentially of 5-acetyl-2,6-dimethylene-10,10-dimethylbicyclo [7.2.0$^{1,9}$] undecane and of 1-acetyl-11-methylene-4,7,7-trimethyl-cycloundeca-4,8-diene comprising treating clove oil with a base, fractionally distilling the treated oil to obtain a terpene fraction having a boiling point of 80° to 110°C/2 Torr and acetylating said terpene fraction under Friedel-Crafts conditions.

2. A perfuming ingredient prepared by reacting with an acetylating reagent in the presence of an acid catalyst under Friedel-Crafts conditions, a terpene fraction having a boiling point of 80°–110°C/2 Torr, said fraction being isolated from clove oil by preliminary treating said oil with a base and subjecting said oil to fractional distillation, said perfuming ingredient comprising of 5-acetyl-2,6-dimethylene-10,10-dimethylbicyclo [7.2.0$^{1,9}$] undecane and of 1-acetyl-11-methylene-4,7,7-trimethyl-cycloundeca-4,8-diene.

3. 5-Acetyl-2,6-dimethylene-10,10-dimethylbicyclo[7.2.0$^{1,9}$]undecane.

* * * * *

UNITED STATES PATENT AND TRADEMARK OFFICE
CERTIFICATE OF CORRECTION

PATENT NO. : 3,966,819
DATED : June 29, 1976
INVENTOR(S) : Karl-Heinrich Schulte-Elte, et al.

It is certified that error appears in the above-identified patent and that said Letters Patent are hereby corrected as shown below:

Column 2, line 6-7 delete "and as flavouring and taste-modifying agents" second occurrence Column 5, line 37 "temperature" should be --temperatures--

Column 6, line 3 "MS: $M^+_\mp$ 246 (1);" should be --

MS: $M^+ =$ 246 (1);--

*Signed and Sealed this*

Twenty-sixth *Day of* October 1976

[SEAL]

*Attest:*

RUTH C. MASON
*Attesting Officer*

C. MARSHALL DANN
*Commissioner of Patents and Trademarks*